United States Patent [19]
Sawaki et al.

[11] Patent Number: 5,954,705
[45] Date of Patent: *Sep. 21, 1999

[54] ABSORBENT ARTICLE

[75] Inventors: Noriko Sawaki; Aki Dokan, both of Higashinada-ku, Japan

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/983,060

[22] PCT Filed: Jun. 3, 1996

[86] PCT No.: PCT/US96/10172

§ 371 Date: Dec. 12, 1997

§ 102(e) Date: Dec. 12, 1997

[87] PCT Pub. No.: WO96/41602

PCT Pub. Date: Dec. 27, 1996

[30] Foreign Application Priority Data

Jun. 13, 1995 [JP] Japan ................................. 7-146233

[51] Int. Cl.⁶ .................................................. A61F 13/15
[52] U.S. Cl. ........................ 604/385.1; 604/378; 604/387
[58] Field of Search ................................ 604/378, 385.1, 604/386, 387

[56] References Cited

U.S. PATENT DOCUMENTS

| | | |
|---|---|---|
| 3,071,138 | 1/1963 | Garcia . |
| 3,653,382 | 4/1972 | Easley et al. . |
| 3,954,107 | 5/1976 | Chesky et al. . |
| 4,340,058 | 7/1982 | Pierce et al. . |
| 4,973,325 | 11/1990 | Sherrod et al. . |
| 4,988,344 | 1/1991 | Reising et al. . |
| B1 4,589,876 | 5/1986 | Van Tilburg . |

FOREIGN PATENT DOCUMENTS

WO 93/21879  11/1993  WIPO .
WO 95/27457  10/1995  WIPO .

*Primary Examiner*—John G. Weiss
*Assistant Examiner*—Dennis Ruhl
*Attorney, Agent, or Firm*—Theodore P. Cummings; Jeffrey V. Bamber; Jacobus C. Rasser

[57] ABSTRACT

An absorbent article comprising a liquid pervious topsheet (4), a liquid impervious backsheet, and an absorbent core (8) surrounded by the topsheet (4) and the backsheet is improved in such a manner as to be deformed in the width direction without being distorted inappropriately when undergoing a widthwise compressive force. The absorbent core (8) includes a central core piece (12) and a pair of side core pieces (14) disposed on both sides of the central core piece; or includes a central core portion, a pair of connecting portions extending downwardly from the opposite side edges of the central core portion, and a pair of side core portions extending widthwise outwardly from the connecting portions. When a widthwise compressive force is exerted, the side core pieces or the side core portions are displaced widthwise inwardly and caused to sink below the central core piece or the central core portion.

4 Claims, 6 Drawing Sheets

ABSORBENT ARTICLE

FIELD OF THE INVENTION

This invention relates to a disposable absorbent article, and more particularly, to a disposable absorbent article having a liquid pervious topsheet, a liquid impervious backsheet, and an absorbent core surrounded by the topsheet and the backsheet.

The term "absorbent articles" as used herein refers to sanitary napkins, pantiliners, and incontinence pads designed to absorb and retain body fluids, such as menses and urine, discharged from the human body when they are worn so as to cover the urogenital region.

BACKGROUND OF THE INVENTION

As is well known, an absorbent article advantageously used as a sanitary napkin has a liquid pervious topsheet, a liquid impervious backsheet, and an absorbent core surrounded by the topsheet and the backsheet. It is important that such an absorbent article be appropriately positioned relative to the wearer's urogenital region, and should have the core absorb body fluids, discharged from the wearer, through the topsheet, and hold them without allowing their leakage to the surroundings. Generally, while the wearer is in motion, such as when walking, sitting down, or standing up, the wearer's thighs are closed, and a widthwise compressive force is exerted on the absorbent article. As a result, the absorbent article is irregularly distorted and folded with respect to its longitudinal central axis. Owing to this phenomenon, body fluids discharged cannot be appropriately absorbed and held by the core any longer. The body fluids tend to leak, particularly, to the widthwise opposite sides. Leakage to the widthwise opposite sides called lateral leakage, if any, stains the wearer's skin with the body fluids, and accordingly, the wearer's clothing, such as panties.

The term "longitudinal" as used herein refers to a direction extending on the front and back of the body along the absorbent article worn in a required state covering the wearer's urogenital region (a direction extending substantially horizontally in the back-and-forth direction of the body when the absorbent article is laid, in a flat form, substantially horizontally below the crotch region of the body standing upright). The term "widthwise" as used herein refers to a direction extending on the right and left of the body along the absorbent article worn in a required state covering the wearer's urogenital region (a direction extending substantially horizontally in the right-and-left direction of the body when the absorbent article is laid, in a flat form, substantially horizontally below the crotch region of the body standing upright).

Conventional attempts to prevent the leakage of body fluids to the widthwise opposite sides that is ascribed to the compression of the absorbent article in the width direction include, for example, constructing the absorbent core from a plurality of core pieces laid in layers in the up-and-down direction and/or arranged side by side in the width direction. Such conventional attempts are disclosed in Japanese Laid-Open Patent Publication Nos. 5-115506 and 5-84261, Japanese Laid-Open Utility Model Publication No. 5-28327, British Patent 23,103, and U.S. Pat. Nos. 3,071,138, 3,653, 382, 3,954,107, 4,340,058, 4,589,876, 4,973,325 and 4,988, 344.

The conventional absorbent article having the core constructed from the plurality of core pieces poses the problem that the leakage of body fluids to the widthwise opposite sides cannot be prevented fully satisfactorily, and/or the structure is considerably complicated and the cost of manufacturing is high. The present invention has been accomplished in the light of the above-mentioned facts.

It is, therefore, an object of the present invention to provide a novel and improved absorbent article which, when undergoing a widthwise compressive force, is deformed in the width direction without being distorted inappropriately, whose required site is kept at the required position of the wearer's urogenital region, and which thus prevents the widthwise bilateral leakage of body fluids fully satisfactorily.

It is another object of the present invention to provide a novel and improved absorbent article which, although being producible for a relatively low cost and with a relatively simple structure, prevents the widthwise leakage of body fluids fully satisfactorily, even when a widthwise compressive force is exerted thereon.

SUMMARY OF THE INVENTION

According to a first aspect of the present invention, an absorbent core is composed of a central core piece and a pair of side core pieces disposed on both sides of the central core piece, and when a widthwise compressive force is exerted, each of the side core pieces is displaced widthwise inwardly and caused to sink below the central core piece.

That is, according to the first aspect of the present invention, an absorbent core is provided which comprises a liquid pervious topsheet, a liquid impervious backsheet, and an absorbent core surrounded by the topsheet and the backsheet, wherein the absorbent core includes a central core piece and a pair of side core pieces disposed on both sides of the central core piece, and when a widthwise compressive force is exerted, each of the side core pieces is displaced widthwise inwardly and caused to sink below the central core piece.

Preferably, the lower surface of each of the side core pieces is joined to the backsheet, and on the outer surface of the backsheet is disposed, in an area extending along the lower surface of each of the side core pieces, a bonding means for strippably bonding the backsheet to the inner surface of panties. Preferably, a liquid impervious intermediate sheet for preventing a liquid flow from the central core piece to each of the side core pieces is disposed between the central core piece and each of the side core pieces. Preferably, each of the intermediate sheets extends, in a widthwise sectional view, along a side edge portion of the upper surface, the side surface, and a side edge portion of the lower surface of the central core piece, then extends widthwise outwardly from the side edge portion of the lower surface of the central core piece to the lower surface of each of the side core pieces, and is joined not only to the side edge portion of the upper surface and the side edge portion of the lower surface of the central core piece, but also to the lower surface of the side core piece. The widthwise dimension of each of the intermediate sheets may be set at such a dimension that each of the side core pieces is prevented from sinking below the central core piece in the entire width direction, especially, such a dimension that more than the widthwise inward half of each of the side core pieces is prevented from sinking below the central core piece. Preferably, each of the side core pieces is joined to the backsheet via the intermediate sheet. The topsheet includes a central topsheet piece and a pair of side topsheet pieces, the central topsheet piece covers at least the upper surface of the central core piece, and each of the side topsheet pieces covers at least the upper surface of each of the side core pieces. Preferably, widthwise opposite side portions of the central topsheet piece extend, in a widthwise sectional view, along opposite side edge portions of the upper surface, the opposite side surfaces, and the opposite side edges of the lower surface, of the central core piece, outwardly of each of the intermediate sheets, and a widthwise inward portion of the side topsheet piece extends, in the widthwise sectional view, along the widthwise inward side surface and the lower surface of the side core piece. Alternatively, the topsheet is formed of a single'sheet piece covering at least the upper surface of the central core piece and the upper surface of each of the side core pieces. In a state before the widthwise compressive force is exerted, the widthwise inward edge of each of the side core pieces is located adjacently to and widthwise outwardly of each of the opposite side edges of the central core piece. Alternatively, in a state before the widthwise compressive force is exerted, a widthwise inward edge portion of each of the side core pieces is located below each of opposite side edge portions of the central core piece. The width of the central core piece is 5 to 100 mm, preferably 20 to 70 mm, more preferably 30 to 50 mm. The width of each of the side core pieces is 2 to 50 mm, preferably 5 to 35 mm, more preferably 8 to 18 mm.

According to a second aspect of the present invention, an absorbent core is adopted which includes a central core portion, a pair of connecting portions extending downwardly from the opposite side edges of the central core portion, and a pair of side core portions extending widthwise outwardly from the lower end of each of the connecting portions, and when a widthwise compressive force is exerted, each of the side core portions is displaced widthwise inwardly and caused to sink below the central core.

That is, according to the second aspect of the present invention, an absorbent core for solving the technical challenge is provided which comprises a liquid pervious topsheet, a liquid impervious backsheet, and an absorbent core surrounded by the topsheet and the backsheet, wherein the absorbent core includes a central core portion, a pair of connecting portions extending downwardly from the opposite side edges of the central core portion, and a pair of side core portions extending widthwise outwardly from the lower end of each of the connecting portions, and when a widthwise compressive force is exerted, each of the side core portions is displaced widthwise inwardly and caused to sink below the central core.

Preferably, the lower surface of each of the side core portions of the absorbent core is joined to the backsheet, and on the outer surface of the backsheet is disposed, in an area extending along the lower surface of each of the side core portions, a bonding means for strippably bonding the backsheet to the inner surface of panties. Preferably, each of the connecting portions of the absorbent core extends downwardly in a widthwise inwardly inclined manner, and the absorbent core is in the shape of __ as a whole. Preferably, a pair of liquid impervious intermediate sheets covering opposite side edge portions of the upper surface of the central core portion of the absorbent core and covering the outer surface of each of the connecting portions are disposed, and the topsheet is disposed outside each of the intermediate sheets. Alternatively, it is preferred that a pair of liquid impervious intermediate sheets covering opposite side portions of the upper surface of the central core portion of the absorbent core, the outer surface of each of the connecting portions, and the upper surfaces of the side core portions are disposed; an absorbent auxiliary core piece is disposed on the upper surface of that portion of each of the intermediate sheets which covers the upper surface of the side core portion; and the topsheet is disposed outside each of the intermediate sheets and the auxiliary core pieces. Preferably, the width of the central core portion is 5 to 120 mm, particularly 25 to 80 mm, more particularly 35 to 60 mm. Preferably, the width of each of the side core portions is 2 to 60 mm, particularly 5 to 40 mm, more particularly 8 to 25 mm.

In the absorbent article constituted according to the first aspect of the present invention, when a widthwise compressive force is exerted on it owing to the wearer's motion, the side core pieces are displaced widthwise inwardly and caused to sink below the central core piece. As a result, the absorbent article is effectively prevented from being irregularly distorted with respect to its longitudinal axis, so that the central core piece is maintained at an appropriate position relative to the wearer's urogenital region. Since the side core pieces are caused to sink below the central core piece, moreover, the central core portion is brought into more intimate contact with the wearer's urogenital region. Upon release of the widthwise compressive force, the side core pieces are moved toward their original positions.

In the absorbent article constituted according to the second aspect of the present invention, when a widthwise compressive force is exerted on it owing to the wearer's motion, the side core portions are displaced widthwise inwardly and caused to sink below the central core portion. As a result, the absorbent article is effectively prevented from being irregularly distorted with respect to its longitudinal axis, so that the central core portion is maintained at an appropriate position relative to the wearer's urogenital region. Since the side core portions are caused to sink below the central core portion, moreover, the central core portion is brought into more intimate contact with the wearer's urogenital region. Upon release of the widthwise compressive force, the side core portions are moved toward their original positions.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Preferred embodiments of the present invention will be described in more detail with reference to the accompanying drawings. These drawings illustrate a sanitary napkin, a preferred embodiment of an absorbent article constructed in accordance with the present invention. Of the drawings, sectional views (FIGS. 3 to 9) show the thicknesses of the constituent elements, and/or the distances in the direction of thickness (i.e. the up-and-down direction in FIGS. 3 to 9) between the constituent elements, in a considerably exaggerated manner in order to clearly indicate how these constituent elements are laminated and joined to one another.

Figure 1:
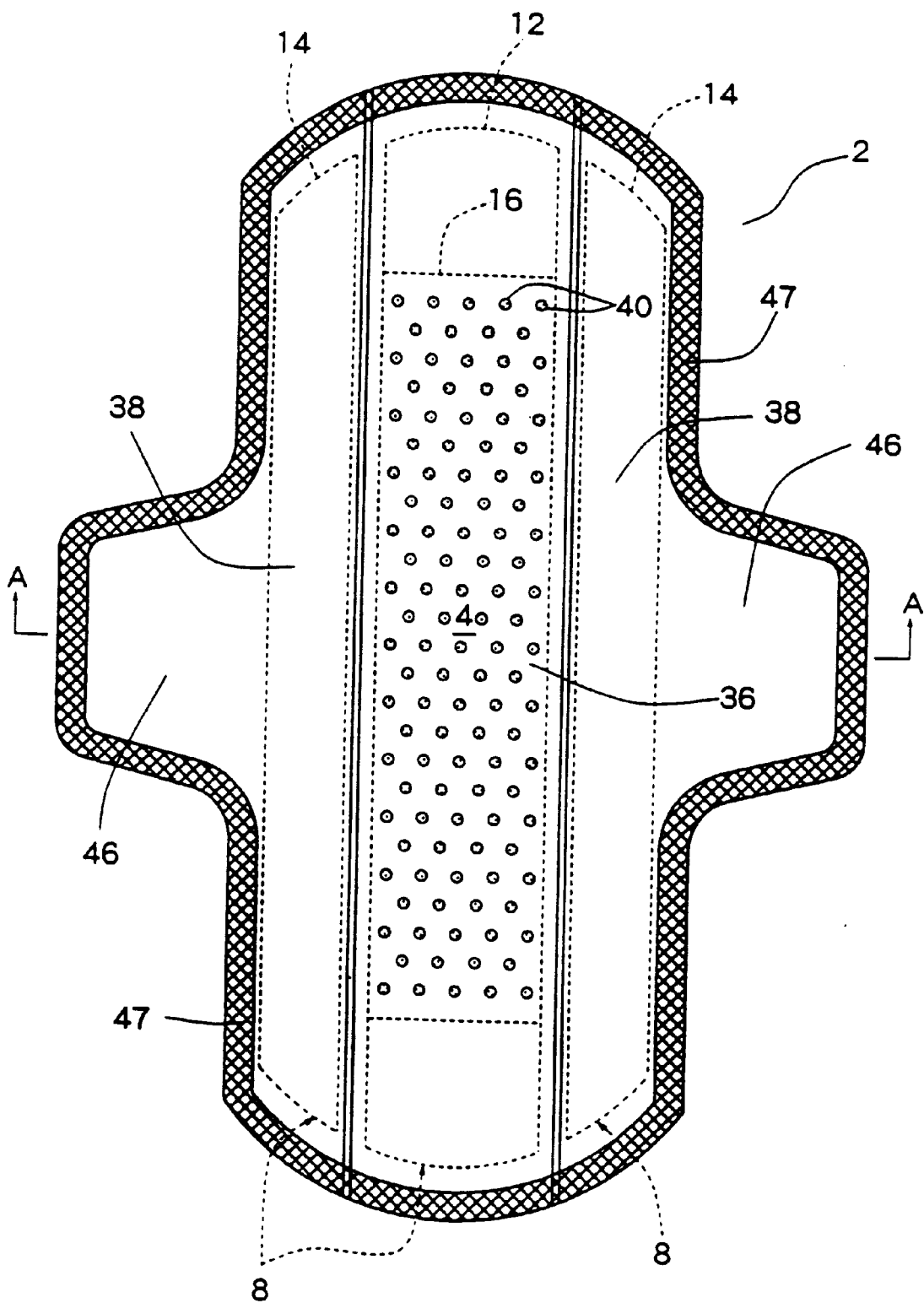
FIG. 1 is a plan view of a sanitary napkin as a preferred embodiment of an absorbent article constructed in accordance with the present invention.
Figure 2:
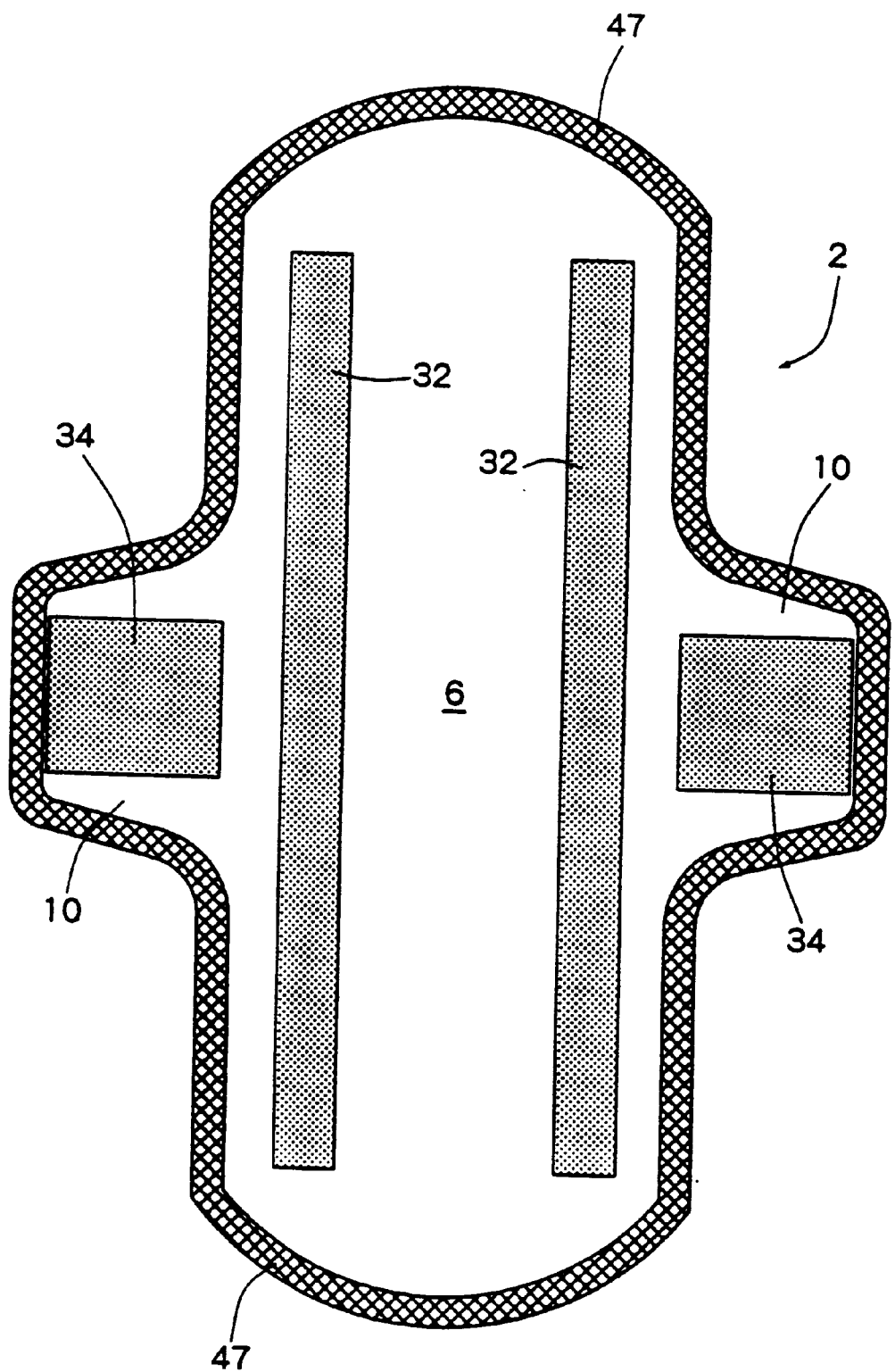
FIG. 2 is a bottom view of the napkin shown in FIG. 1.
Figure 3:
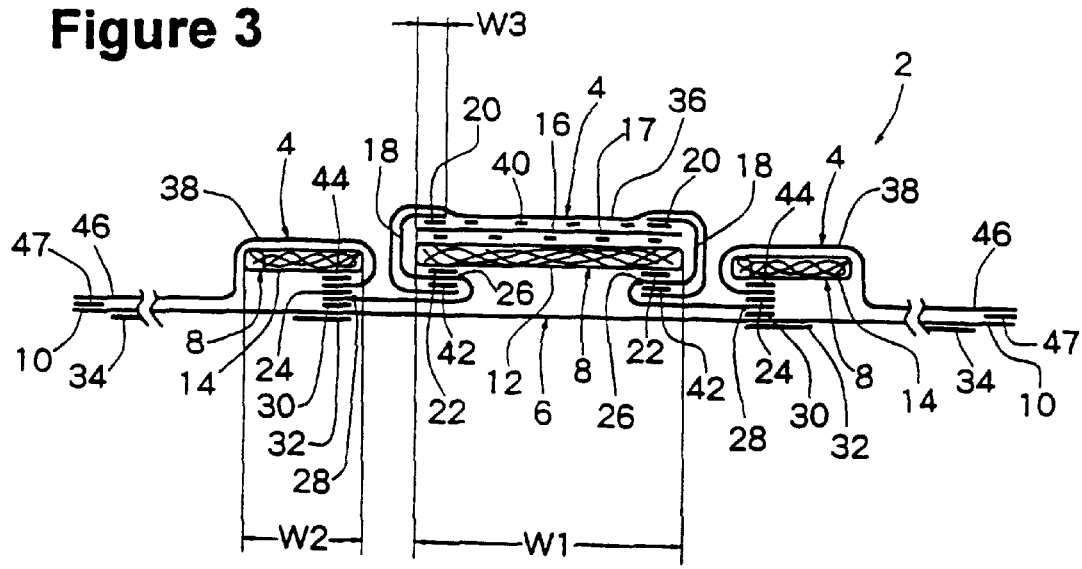
FIG. 3 is a sectional view taken on line A—A of FIG. 1.

FIGS. 1 to 3 show a sanitary napkin, an embodiment of an absorbent article constructed in accordance with the present invention. The napkin shown entirely at the numeral 2 has a liquid pervious topsheet 4, a liquid impervious backsheet 6, and an absorbent core 8 surrounded by the topsheet 4 and the backsheet 6.

The backsheet 6 is formed entirely of a single piece, and as seen from FIG. 2, is nearly rectangular as a whole. The opposite edges in the longitudinal direction (in the up-and-down direction in FIG. 2) of the backsheet 6 are in a convexly arcuate form. At a longitudinally central portion of the backsheet 6 are formed a pair of wing portions 10 protruding in the width direction (the right-and-left direction in FIGS. 2 and 3). Each of the wing portions may be nearly in the shape of a trapezoid whose longitudinal dimension is gradually decreased widthwise outwardly. The backsheet 6 can be advantageously formed from a flexible liquid impervious thermoplastic film such as a polyolefinic film. Particularly preferred films for forming the backsheet 6 include a low density polyethylene film 0.01 to 0.05 mm, particularly, about 0.025 mm, in thickness. Such a polyethylene film is sold by the Ethyl Corp., Visqueen Division, as Model XP-39385 and by the Clopay Corp. of Cincinnati, Ohio, USA, as SOFFLEX 1401.

In the illustrated embodiment, the absorbent core 8 includes three core pieces, i.e., a central core piece 12 and a pair of side core pieces 14. The pair of side core pieces 14 are arranged side by side on both sides of the central core piece 12, with the widthwise inward edge of each of them being adjacent to the side edge of the central core piece 12. As will be seen by reference to FIG. 1, the central core piece 12 and the pair of side core pieces 14 cooperatively define a shape nearly similar to, and slightly small than, the shape of a main portion of the backsheet 6, i.e., the portion excluding the pair of wing portions 10. The central core piece 12 is relatively broad, and the side core pieces 14 are relatively less broad. Preferably, the width, W1, of the central core piece 12 is 5 to 100 mm, particularly 20 to 70 mm, and more particularly 30 to 50 mm. If the width W1 of the central core piece 12 is too large, the tendency arises, as will be mentioned later, that when a widthwise compressive force is exerted on the napkin 2, the central core piece 12 itself is irregularly distorted with respect to the longitudinally central axis. Body fluids discharged from the wearer are to be absorbed and held by the central core piece 12. If the width W1 of the central core piece 12 is too small, the body fluids absorbing and holding capacities of the central core piece 12 will become insufficient. The width, W2, of the side core piece 14 is set according to the width W1 of the central core piece 12 and the width of the main portion of the backsheet 8. Preferably, it is 2 to 50 mm, particularly 5 to 35 mm, and more particularly 8 to 18 mm. If desired, the central core piece 12 may be rendered relatively thick to increase its body fluids absorbing and holding capacities. Also, the side core piece 14 may be relatively thin so that it can sink below the central core piece 14 more smoothly. The central core piece 12 and the pair of side core pieces 14 can be advantageously formed from materials, such as comminuted wood pulp called airfelt; creped cellulose wadding; meltblown polymers; chemically stiffened, modified, or crosslinked cellulosic fibers; absorbent plastic foams; layers of tissue paper; absorbent gelling materials (materials gelling when absorbing liquids); or any suitable combinations of these.

On the upper surface of the central core piece 12 is disposed a dispersing sheet 16 generally called a secondary topsheet. The dispersing sheet 16 desirably has the function to disperse a body fluid, which has passed through the topsheet 4, in the longitudinal direction and cause it to be absorbed by the central core piece 12. Preferably, the dispersing sheet 16 can be formed from a nonwoven fabric of natural or synthetic fiber. Particularly preferred nonwovens for forming the dispersing sheet 16 include a nonwoven fabric of spunbond polypropylene fibers designated P-9 available from the Fiberweb Corporation of Simpsonville, S.C., USA, under the tradename CELESTRA; and a nonwoven fabric formed of bicomponent fibers which have a polyethylene sheath and a polyester core or a polyethylene sheath and a polypropylene core, the fabric available from the Havix Company, of Japan, as S2146. The dimension in the width direction (the right-and-left direction in FIGS. 1 and 3) of the dispersing sheet 16 is substantially the same as the widthwise dimension of the central core piece 12. The dimension in the longitudinal direction (the up-and-down direction in FIG. 1) of the dispersing sheet 16 is somewhat smaller than the longitudinal dimension of the central core piece 12. The longitudinally opposite edges of the dispersing sheet 16 are positioned inwardly of the longitudinally opposite edges of the central core piece 12. The dispersing sheet 16 is joined to the upper surface of the central core piece 12 in a multiplicity of discrete areas of bonding 17 using an adhesive. In FIG. 3, the areas of bonding 17 between the central core piece 12 and the dispersing sheet 16 are indicated by heavy solid lines for convenience of illustration. Instead of providing the multiplicity of discrete areas of bonding 17, there may be disposed an areas of bonding which, for example, extends uninterruptedly in a spiral manner. If desired, the dispersing sheet 16 may be joined to the central core piece 12 by ultrasonic welding or thermal bonding rather than the use of an adhesive. Furthermore, the dispersing sheet may be disposed not only on the upper surface of the central core piece 16, but also on the upper surfaces of the side core pieces 14.

With reference to FIG. 3, a liquid impervious intermediate sheet 18 is interposed between the central core piece 12 and each of the pair of side core pieces 14. Each of the intermediate sheets 18 extends, in a widthwise sectional view, i.e., in FIG. 3, along a side edge portion of the upper surface of the central core piece 12 (accordingly, a side edge portion of the upper surface of the dispersing sheet 16), its side surface, and a side edge portion of its lower surface, is then folded back, and extends widthwise outwardly from the side edge portion of the lower surface of the central core piece 12 to the lower surface of the side core piece 14. The widthwise outward edge of the intermediate sheet 18 is positioned at a widthwise central portion on the lower surface of the side core piece 14. Each of the intermediate sheets 18 is caused to extend longitudinally throughout the length of the napkin 2, and the longitudinally opposite edges of each of the intermediate sheets 18 are aligned with the longitudinally opposite edges of the backsheet 6. Each of the intermediate sheets 18 is bonded, using an adhesive, to the central core piece 12 in areas of bonding 20 and 22, and to the side core piece 14 (via a side topsheet piece to be described later) in areas of bonding 24, the areas of bonding being schematically represented by heavy solid lines in FIG. 3. More specifically, the intermediate sheet 18 is bonded to the side edge portion of the upper surface of the dispersing sheet 16 in the area of bonding 20, accordingly bonded to the side edge portion of the upper surface of the central core piece 12 via the dispersing sheet 16, is then bonded to the side edge portion of the lower surface of the central core piece 12 in the area of bonding 22, and is finally bonded to the lower surface of the side core piece 14 (via a side topsheet piece to be described later) in the area of bonding 24. The areas of bonding 20, 22 and 24 are preferably caused to extend longitudinally uninterruptedly throughout the lengths of the central core piece 12 and the side core piece 14. If desired, each of the areas of bonding 20, 22 and 24 may be converted into a multiplicity of discrete areas. Moreover, the intermediate sheet 18 may be bonded, using ultrasonic welding or thermal bonding rather than an adhesive, to the central core piece 12, and to the side core piece 14 (via the side topsheet piece to be described later). The width, W3, of that portion of the intermediate sheet 18 which lies over the side edge portion of the central core piece 12 is preferably as small as 2 to 3 mm. If this width W3 is large, penetration of a body fluid into the central core piece 12 will be considerably hampered because of the presence of the liquid impervious intermediate sheet 18. If the intermediate sheet 18 does not exist at the side edge portion of the central core piece 12, a body fluid absorbed by the central core piece 12 will directly leak widthwise outwardly from the upper surface of the central core piece 12, particularly when the napkin 2 undergoes a widthwise compressive force. The body fluid will flow widthwise to the side core piece 14, arousing the possibility for its lateral leakage. As will be noted later, when the widthwise compressive force acts on the napkin 2, the pair of side core pieces 14 are displaced widthwise inwardly and caused to sink below the central core piece 12. Such sinking is limited by the widthwise length of that portion of the intermediate sheet 18 which ranges from the site indicated by the numeral 26 to the site indicated by the numeral 28. This widthwise length from the site 26 to the site 28 of the intermediate sheet 18 is preferably such a dimension that the whole of the side core piece 14 in the width direction is kept from sinking below the central core piece 12, in other words, that when the side core piece 14 is displaced to the widthwise innermost position, the widthwise outward edge of the side core piece 14 is limited to a position, even slightly, widthwise outwardly of the widthwise outward edge of the central core piece 12. Particularly preferably, that length is set at such a dimension that more than the inward half of the side core piece 14 is prevented from sinking below the central core piece 12, in other words, that when the side core piece 14 is displaced to the widthwise innermost position, the widthwise nearly half of the side core piece 14 is limited to a state extruding widthwise outwardly of the central core piece 12. Importantly, the intermediate sheet 18 is liquid impervious, and can be formed preferably of substantially the same material as that of the backsheet 6, namely, a flexible liquid impervious thermoplastic film, especially, a low density polyethylene film 0.01 to 0.05 mm, particularly, about 0.025 mm, in thickness.

In an area of bonding 30 schematically represented by a heavy solid line in FIG. 3, thz lower surface of the intermediate sheet 18 is bonded to the upper surface or inner surface of the backsheet 6 using an adhesive. Preferably, the area of bonding 30 is located below the side core piece 14 in alignment with the area of bonding 24 between the intermediate sheet 18 and the lower surface of the side core piece 14 (via the side topsheet to be described later). Thus, the side core piece 14 is joined to the backsheet 6 via the side topsheet (to be described) and the intermediate sheet 18. Preferably, the area of bonding 30 is not present below the central core piece 12. The area of bonding 30 between the intermediate sheet 18 and the backsheet 6 can be caused to extend longitudinally uninterruptedly throughout the length of the intermediate sheet 18, or a plurality of discrete areas of bonding 30 may be arranged longitudinally. If desired, the intermediate sheet 18 can be joined to the backsheet 6 by ultrasonic welding or thermal bonding instead of using an adhesive. On the lower surface or outer surface of the backsheet 6 is disposed a bonding means 32 for strippably bonding the backsheet 6 to the inner surface of panties. For convenience's sake, an area where the bonding means 32 is applied is indicated by many dots in FIG. 2, and represented by a heavy solid line in FIG. 3. As will be stated later, when the wearer's thighs are closed to exert a widthwise compressive force on the napkin 2, the side core piece 14 needs to be smoothly displaced widthwise inwardly attendant on the displacement of the wearer's panties, thereby causing it to sink below the central core piece 12. For this purpose, it is preferred that the bonding means 32 be disposed below the side core piece 14, but not below the central core piece 12. As will be seen clearly from FIGS. 2 and 3, a bonding means 34 is also provided on the outer surface or lower surface of each of the pair of wing portions 10 of the backsheet 6. The bonding means 32 and 34 may be composed advantageously of a pressure sensitive adhesive. A pressure sensitive adhesive that can be used preferably is Century Adhesive A-305-IV sold by Century Adhesive Corp. of Columbus, Ohio, USA. For purposes of, say, preventing the soiling of the pressure sensitive adhesive prior to use, it is desirable to cover it strippably with a silicone coated paper (not shown). If desired, other bonding means, such as a double-sided adhesive tape, may be used instead of the pressure sensitive adhesive.

If desired, the above-described intermediate sheet 18 may be omitted from the viewpoint of, say, reduction in the manufacturing cost. In this case, a hydrophobic treatment well known per se can be applied, where necessary, to a widthwise inward region of the side core piece 14 in order to prevent a body fluid absorbed by the central core piece 12 from flowing widthwise into the side core piece 14 directly from the central core piece 12 and further flowing widthwise through the side core piece 14.

With reference to FIGS. 1 and 3, the topsheet 4 in the illustrated embodiment includes a central topsheet piece 36 and a pair of side topsheet pieces 38. The central topsheet piece 36 has, in a widthwise sectional view, i.e., FIG. 3, a main portion covering the upper surface of the dispersing sheet 16 disposed on the upper surface of the central core piece 12, and a portion extending along opposite side portions, the opposite side surfaces, and opposite side portions of the lower surface of the central core piece 12 outwardly of the intermediate sheet 18. The main portion of the central topsheet piece 36, i.e., that portion covering the dispersing sheet 16, is thermally bonded to the dispersing sheet 16 in a multiplicity of areas of thermal bonding 40 arranged at intervals. For convenience's sake, the areas of thermal bonding 40 are indicated by many dots in FIG. 1, and by heavy solid lines in FIG. 3. Opposite side edge portions of the central topsheet piece 36 are bonded, using an adhesive, to that portion of the intermediate sheet 18 which covers the lower surface of the central core piece 12 (in other words, to the lower surface of the central core piece 12 via the intermediate sheet 18), in areas of bonding 42 indicated by heavy solid lines in FIG. 3. The areas of bonding 42 are caused to extend longitudinally uninterruptedly throughout the lengths of the central topsheet piece 36 and the intermediate sheet 18. If desired, the main portion of the central topsheet piece 36 may be joined to the dispersing sheet 16 by using an adhesive or by ultrasonic welding. Moreover, the opposite side edge portions of the central topsheet piece 36 may be joined to the intermediate sheet 18 by ultrasonic welding or thermal bonding. The areas of bonding 42 between the opposite side edge portions of the central topsheet piece 36 and the intermediate sheet 18 may be formed into a multiplicity of discrete areas.

Each of the side topsheet pieces 38 extends, in a widthwise sectional view, i.e., FIG. 3, along the widthwise inward half of the lower surface of the side core piece 14, then along the widthwise inward side surface of the side core piece 14, and further along the upper surface and the widthwise outward side surface of the side core piece 14, and finally extends widthwise outwardly. A widthwise inward edge portion of the side topsheet piece 38 is bonded, using an adhesive, to the lower surface of the side core piece 14 in an area of bonding 44 indicated by a heavy solid line in FIG. 3. (The widthwise outward edge portion of the intermediate sheet 18 is bonded to the side topsheet piece 38 in the area of bonding 24, and bonded to the lower surface of the side core piece 14 via the side topsheet piece 38.) The area of bonding 44 extends longitudinally uninterruptedly throughout the length of the side core piece 14. If desired, the area of bonding 44 may be formed into a multiplicity of discrete areas. The widthwise inward edge portion of the side topsheet piece 38 may be joined to the lower surface of the side core piece 14 by ultrasonic welding or thermal bonding rather than by use of an adhesive. In the illustrated embodiment, the upper surface of the side core piece 14 and the side topsheet piece 38 are not joined to each other. If desired, however, the side topsheet piece 38 may be joined to the upper surface of the side core piece 14, as is the upper surface of the central core piece 12 to the central topsheet piece 36, by a suitable method, such as bonding in a multiplicity of areas of bonding arranged at intervals.

As will be understood clearly by reference to FIG. 1, the central topsheet piece 36 and the pair of side topsheet pieces 38 cooperatively define, in the plan view, substantially the same shape as that of the backsheet 6. At a longitudinally central portion of each of the side topsheet pieces 38 is formed a wing portion 46 of substantially the same shape as the wing portion 10 of the backsheet 6. The central topsheet piece 36 and the side topsheet pieces 38 are thermally bonded to the backsheet 6 uninterruptedly along the entire outer peripheral edge of the napkin 2. For convenience of illustration, such areas of thermal bonding 47 are represented by intersecting diagonal lines in FIGS. 1 and 2, and heavy solid lines in FIG. 3. The thermal bonding procedure is usually performed after all the constituent elements making up the napkin 2 are disposed relative to one another as required. Thus, the longitudinally opposite end portions of the intermediate sheet 18, located at the outer peripheral edge portion of the backsheet 6, are also thermally bonded to the backsheet 6, central topsheet piece 36 and side topsheet pieces 38. The central topsheet piece 36 and side topsheet pieces 38, importantly, should be liquid pervious, and should not cause excessive discomfort to the wearer when they are contacted with the wearer's skin. The central topsheet piece 36 and side topsheet pieces 38 can be formed advantageously from materials, such as woven or nonwoven fabrics of natural or synthetic fibers; apertured thermoplastic films; porous plastic foams; reticulated thermoplastic films; and thermoplastic scrims. Particularly advantageous materials are apertured polyolefinic films as disclosed in U.S. Pat. Nos. 3,929,135, 4,324,246, 4,342,314, 4,463,045 and 5,006,394.

Figure 4:
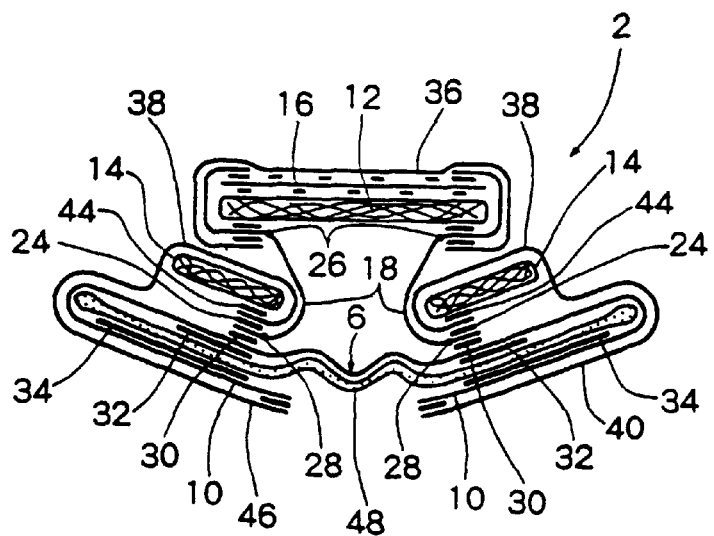
FIG. 4 is a sectional view similar to FIG. 3, showing the napkin of FIG. 1 along with part of panties in a state in which a widthwise compressive force is exerted.

The above-described napkin 2 is used as an overlay on a required site of the inner surface of the wearer's panties 48 (partly shown in FIG. 4). For use, the external surface of the backsheet 6 is attached strippably to the internal surface of the panties 48 via the bonding means 32. A pair of wings defined by the pair of wing portions 10 of the backsheet 6, and the wing portions 46 of the pair of side topsheet pieces 38 are folded back on the outside surface of the panties 48. The outer surfaces of the pair of wing portions 10 of the backsheet 6 are attached strippably to the outside surface of the panties 48 via the bonding means 34. Assume that the wearer wears, as required, the panties 48 bearing the napkin 2 at a required site of its inner surface. When a widthwise compressive force is exerted on the napkin 2, for example, by closure of the wearer's thighs, as will be seen by reference to FIG. 4 along with FIG. 3, the side core pieces 14 are displaced widthwise inwardly, and caused to sink below the central core piece 12. The side core piece 14 is bonded to the panties 48 via the bonding means 32 disposed on the outer surface of the backsheet 6 (more specifically, via the area of bonding 44, side topsheet piece 38, area of bonding 24, intermediate sheet 18, area of bonding 30, backsheet 6, and bonding means 32). The side core piece 14 is displaced attendant on the widthwise inward displacement of the panties 48, while the central core piece 12 is not directly joined to the panties 48. Thus, when a widthwise compressive force is exerted on the panties 48 and the napkin 2 by closure of the wearer's thighs, the side core piece 14 is caused to sink below the central core piece 12 fully smoothly when displaced widthwise inwardly. The sinking of the side core piece 14 below it lifts the central core piece 12 somewhat, thereby bringing the widthwise central portion of the napkin 2, i.e., its portion where the central core piece 12 exits, into intimate contact with the wearer's urogenital region. The amount of sinking of the side core piece 14 below the central core piece 12 is restricted, as described previously, by that widthwise length of the intermediate sheet 18 which ranges from the site 26 to the site 28. Since the side core piece 14 sinks below the central core piece 12 to reduce the widthwise dimension of the napkin 2, the phenomenon that the central core piece 12 is irregularly distorted relative to the longitudinally central axis owing to the widthwise compressive force is prevented fully reliably. This leads to preclude the undesirable event that the irregular distortion of the central core piece 12 relative to the longitudinally central axis causes the widthwise central portion of the napkin 2 to be considerably apart from the wearer's urogenital region locally, eventually leaving the wearer's urogenital region locally exposed without being covered by the napkin 2. Upon release of the widthwise compressive force that the napkin 2 has undergone, the napkin 2 is resumed to its initial state or a similar state.

A body fluid such as menses discharged from the wearer penetrates the central topsheet piece 36, reaching the dispersing sheet 16, where it is dispersed longitudinally, and then absorbed and held by the central core piece 12. Since the liquid impervious intermediate sheet 18 exists between the central core piece 12 and the side core piece 14, the body fluid absorbed by the central core piece 12 is not caused to flow from there to the side core piece 14. Even if a considerably large amount of body fluid is discharged, there is no possibility for lateral leakage in which the body fluid flows widthwise through the side core piece 14, leaking outwardly in the width direction. For some reason, a body fluid discharged from the wearer may directly drain widthwise outwardly of the central topsheet piece 36. Such a body fluid is absorbed by the side core piece 14 through the side topsheet piece 38. In this case, therefore, the accident that the body fluid leaks and soils the wearer herself or her clothing such as panties is prevented without fail.

The following modification may be added to the napkin 2 shown in FIGS. 1 to 4 to ensure that when the wearer puts the napkin 2 at a required site of the inside surface of the panties 48 as required, and wears it as required, the widthwise central portion of the napkin 2, i.e., the portion where the central core piece 12 exists, will come into firm intimate contact with the wearer's urogenital region: The central core piece 12, the dispersing sheet 16, the central topsheet piece 36, the intermediate sheet 18, and the widthwise central portion of the backsheet 6 that define the widthwise central portion of the napkin 2 are constituted so as to be elastically substantially inextensible or only slightly extensible. Whereas the side core piece 14, the side topsheet piece 38, and the widthwise opposite side portions of the backsheet 6 that define the widthwise opposite side portions of the napkin 2 are constituted so as to be elastically extensible. By so doing, when the panties 48 with the napkin 2 overlaid as required is worn as required, the widthwise opposite side portions of the napkin are longitudinally elongated according to the longitudinal elongation of the panties 48. Owing to this, the widthwise central portion of the napkin 2, which is substantially inextensible or extensible only slightly, is elastically lifted, and thus brought into fully satisfactorily intimate contact with the wearer's urogenital region. Alternatively, the widthwise central portion of the napkin 2 is constituted so as to be elastically extensible, while its widthwise opposite side portions are constituted so as to be substantially inextensible or only slightly extensible; moreover, a pressure-sensitive adhesive with a relatively high bonding strength may be applied to the longitudinally opposite end portions in the widthwise central portion of the backsheet 6. When such napkin 2 is to be overlaid at a required site of the inner surface of the panties 48, the widthwise central portion of the napkin 2 in an elastically elongated state is engaged with the panties 48 by the bonding means applied to the longitudinally opposite end portions in the widthwise central portion of the backsheet 6. By so doing, elastic shrinkage generated in the widthwise central portion of the napkin 2 causes part of the panties 48 to be pulled longitudinally, and the widthwise central portion of the napkin 2 to be lifted. Thus, when the panties is worn as required, the widthwise central portion of the napkin 2 is brought into fully satisfactorily intimate contact with the wearer's urogenital region. In order that all of the members constituting the napkin 2, or only specific parts of the members constituting the napkin 2 can be elastically elongated, a web material, such as a plastic film, which originally is elastically inextensible or extensible only slightly, is partially machined to deform it into a non-planar shape. For details of such machining, reference is requested to International Publication WP95/03765.

Figure 5:
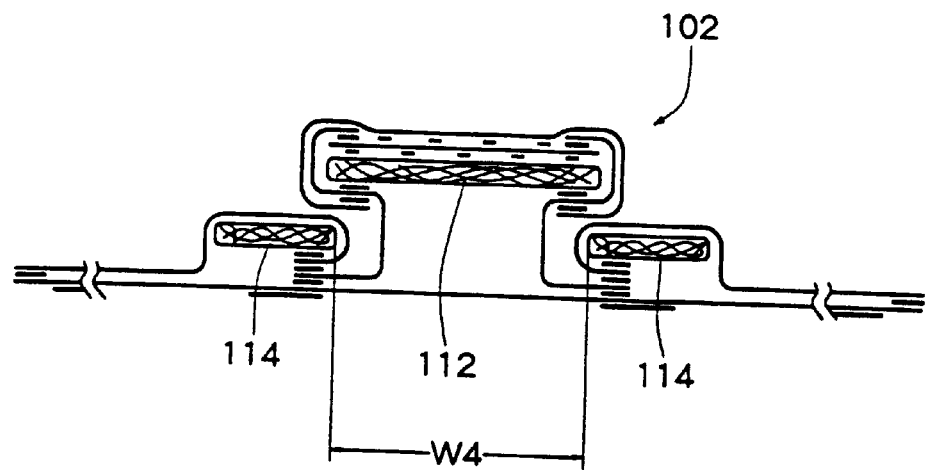
FIG. 5 is a sectional view, similar to FIG. 3, of a modified example of the napkin shown in FIG. 1.

FIG. 5 shows a modified example of the sanitary napkin 2 mentioned above. In a napkin 102 as shown in FIG. 5, when in a state in which no widthwise compressive force is exerted, widthwise inward edge portions of side core pieces 114 have already been caused to sink below widthwise side edge portions of a central core piece 112. The distance, W4, between the pair of side core pieces 114 is somewhat smaller than the width of the central core piece 112. Preferably, the distance W4 between the pair of side core pieces 114 is 2 to 70 mm, particularly 5 to 40 mm, more particularly 10 to 20 mm. In such a napkin 102, when a widthwise compressive force is applied to the napkin 2, the side core pieces 114 are displaced widthwise inwardly more smoothly and caused to sink below the central core piece 112. The structure other than the above-mentioned points of the napkin 102 illustrated in FIG. 5 is substantially the same as that of the napkin 2 shown in FIGS. 1 to 4.

Figure 6:
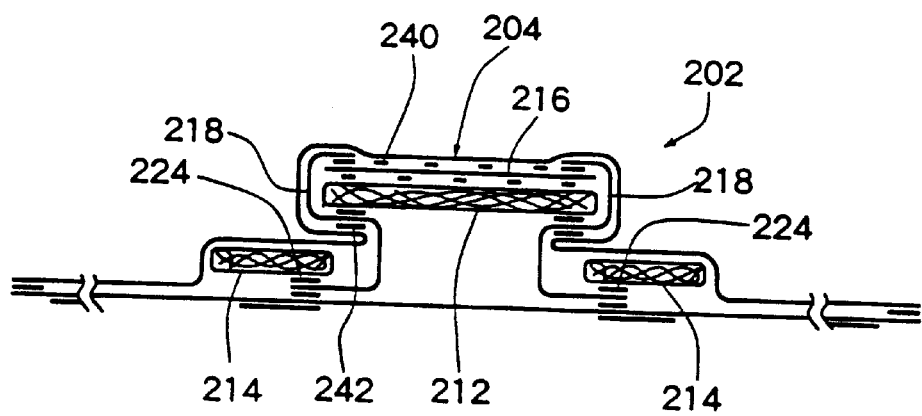
FIG. 6 is a sectional view, similar to FIG. 3, of another modified example of the napkin shown in FIG. 1.

FIG. 6 shows another modified example of the aforementioned sanitary napkin. In a napkin 202 as illustrated in FIG. 6, a topsheet 204 is composed of a single piece. Such a topsheet 204 extends, in a widthwise sectional view, i.e., FIG. 6, widthwise bilaterally side from a main portion covering a dispersing sheet 216 disposed on the upper surface of a central core piece 212, then extends outwardly of an intermediate sheet 218 along opposite side portions, the opposite side surfaces and opposite side portions of the lower surface of the central core piece 212, is then folded back to extend from the lower surface of the central core piece 212, along the upper surface of a side core piece 214 and its widthwise outward side surface, and further extends widthwise outwardly. Such topsheet 204 is thermally bonded to the dispersing sheet 216 in a multiplicity of areas of bonding 240, and bonded, using an adhesive, to that portion of the intermediate sheet 218 which covers the lower surface of the central core piece 212, in an area of bonding 242. In order that when a widthwise compressive force is exerted on the napkin 202, the side core pieces 214 are not kept from being displaced widthwise inwardly and sinking below the central core piece 212, it is important that the topsheet 204 and the side core pieces 214 are not joined to each other. No topsheet 204 exists below the side core piece 214, and the widthwise outward edge portion of the intermediate sheet 218 is bonded, using an adhesive, directly to the lower surface of the side core piece 214 in an area of bonding 224. The structure other than the above-mentioned points of the napkin 202 illustrated in FIG. 6 is substantially the same as that of the napkin 102 shown in FIG. 5.

Figure 7:
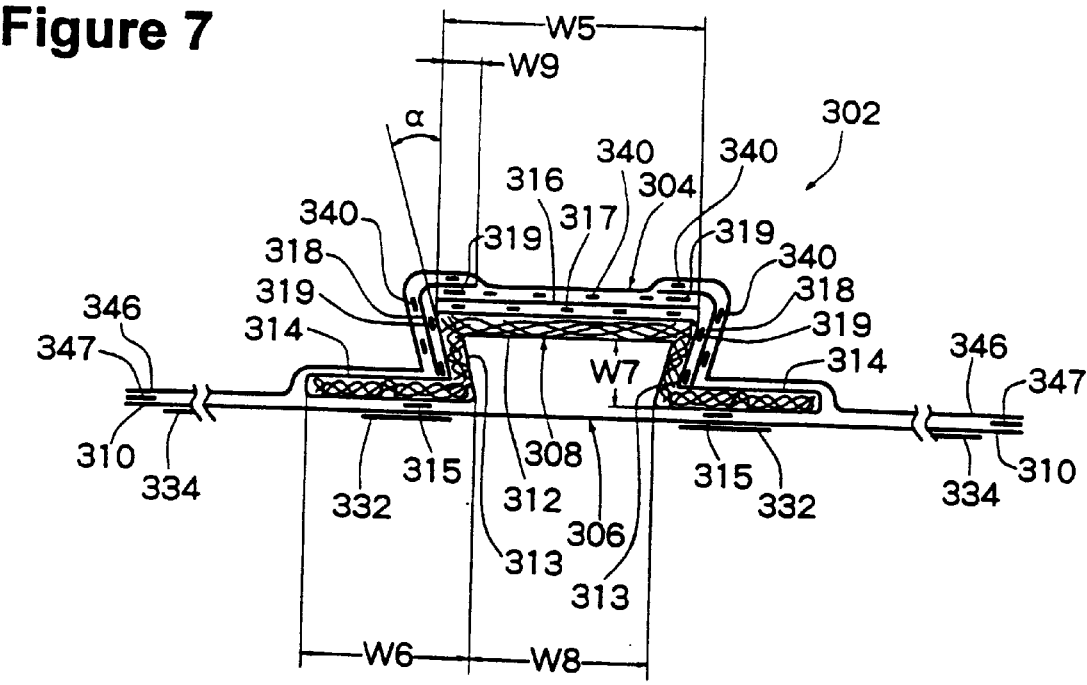
FIG. 7 is a sectional view, similar to FIG. 3, of a sanitary napkin as another preferred embodiment of an absorbent article constructed in accordance with the present invention.

FIG. 7 shows another embodiment of the sanitary napkin constructed in accordance with the present invention. A napkin 302 as shown in FIG. 7 has a liquid pervious topsheet 304, a liquid impervious backsheet 306, and an absorbent core 308 surrounded by the topsheet 304 and the backsheet 306.

The backsheet 306 is substantially the same as the backsheet 106 in the napkin 2 explained with reference to FIGS. 1 to 4. Thus, the backsheet 306 is formed entirely of a single piece, and is nearly rectangular as a whole. The opposite edges in the longitudinal direction (in the direction perpendicular to the sheet face in FIG. 7) of the backsheet 306 are in a convexly arcuate form (reference is requested to FIG. 2 as well) At a longitudinally central portion of the backsheet 306 are formed a pair of wing portions 310 protruding in the width direction (the right-and-left direction in FIG. 7). On the outer surface or lower surface of the backsheet 306 are provided bonding means 332 which are advantageously pressure-sensitive adhesives. The bonding means 332, represented by heavy solid lines for convenience's sake in FIG. 7, are located below a pair of side core portions of an absorbent core 308 to be described in detail later. Also on the lower surfaces or outer surfaces of the pair of wing portions 310 of the backsheet 308 are provided bonding means 334.

In the embodiment illustrated in FIG. 7, the absorbent core 308 is also composed of a single piece. The absorbent core 308 comprises a central core portion 312, a pair of connecting portions 313 extending downwardly from the opposite side edges of the central core portion 312, and a pair of side core portions 314 extending widthwise outwardly from the connecting portions 313. Preferably, each of the connecting portions 313 extends downwardly in a widthwise inwardly inclined manner, and the absorbent core 308 is in the shape of _ as a whole. The central core portion 312 is relatively large in width, while the side core portion 314 is relatively small in width. Preferably, the width, W5, of the central core portion 312 is 5 to 120 mm, particularly 25 to 80 mm, more particularly 35 to 60 mm. Preferably, the width, W6, of the side core portions 314 is 2 to 60 mm, particularly 5 to 40 mm, more particularly 8 to 25 mm. Advantageously, the width, W7, of the connecting portion 313 is 2 to 60 mm, particularly 3 to 35 mm, more particularly 5 to 10 mm. Advantageously, the distance, W8, between the pair of side core portions 314 is 2 to 70 mm, particularly 5 to 40 mm, more particularly 10 to 20 mm. The lower surface of the side core portion 314 in the absorbent core 304 is bonded, using an adhesive, to the upper surface or inner surface of the backsheet 306 in an area of bonding 315 indicated by a heavy solid line for convenience's sake. The area of bonding 315 extends longitudinally (in a direction perpendicular to the sheet face in FIG. 7) uninterruptedly throughout the length of the side core portion 314. The structure other than the above-mentioned points of the absorbent core 308 may be substantially the same as that of the absorbent core 4 in the napkin 2 shown in FIGS. 1 to 4.

On the upper surface of the central core portion 312 in the absorbent core 308 is disposed a dispersing sheet 316. The dispersing sheet 316 may be substantially the same as the dispersing sheet 16 in the napkin 2 illustrated in FIGS. 1 to 4, and is joined to the upper surface of the central core portion 312 of the absorbent core 308, using an adhesive, in a multiplicity of discrete areas of bonding 317 indicated by heavy solid lines for convenience of illustration. Instead of providing the multiplicity of discrete areas of bonding 317, there may be disposed, for example, an area of bonding which extends uninterruptedly in a spiral manner.

On the absorbent core 308 are disposed a pair of liquid impervious intermediate sheets 318. Each of the intermediate sheets extends, in a widthwise sectional view, i.e. FIG. 7, from a side edge portion of the upper surface of the central core portion 312 (accordingly, a side edge portion of the upper surface of the dispersing sheet 316) along the outer surface of the connecting portion 313. In the napkin 302 illustrated in FIG. 7, the absorbent core 308 is formed of a single piece. Thus, as will be mentioned further, when a widthwise compressive force is exerted on the napkin 302 to displace the side core portions 314 widthwise inwardly, causing them to sink below the central core portion 312, the central core portion 312 tends to be deformed in a convexly arcuate form in the widthwise sectional view according to the widthwise inward displacement of the side core portions 314. Owing to this, body fluids are relatively likely to leak directly from the upper surface of the central core portion 312, flowing to the side core portions 314. Hence, the width, W9, of that portion of each of the intermediate sheets 318 which exists at the side edge portion of the central core portion 312 is preferably somewhat larger than the width, W3, of the corresponding portion of the intermediate sheet 18 (FIG. 3.) in the napkin 2 illustrated in FIGS. 1 to 4, and is about 5 to 7 mm. The lower edge of the intermediate sheet 318 is aligned with the lower edge of the connecting portion 313 of the absorbent core 308, and the entire outer surface of the connecting portion 313 of the absorbent core 308 is covered with the intermediate sheet 318. Such intermediate sheet 318 is joined, using an adhesive, to the side edge portion of the upper surface of the central core portion 312 and the outer surface of the connecting portion 313 in the absorbent core 308 in a multiplicity of discrete areas of bonding 319 indicated by heavy solid lines for convenience of illustration. Instead of providing the multiplicity of discrete areas of bonding 319, there may be disposed, for example, an area of bonding which extends uninterruptedly in a spiral manner. If desired, the intermediate sheet 318 may be joined to the absorbent core 308 by ultrasonic welding or thermal bonding. As with the embodiment described by reference to FIGS. 1 to 6, the intermediate sheet 318 may be omitted, if desired, from the aspect of, say, reduction in the manufacturing cost, in the embodiment illustrated in FIG. 7 as well.

The topsheet 304 is also composed of a single piece. It extends, in a widthwise sectional view, i.e., FIG. 7, widthwise bilaterally from a main portion covering the dispersing sheet 316 disposed on the upper surface of the central core portion 312 in the absorbent core 308, then extends outwardly of the intermediate sheet 318 along opposite side portions of the central core portion 312, down the connecting portion 313 and along the side core portion 314, and further extends widthwise outwardly. When viewed in a plan view, the topsheet 304 assumes substantially the same shape as the backsheet 306. In correspondence with the pair of wing portions 310 of the backsheet 306, the topsheet 304 also has a pair of wing portions 346. Such topsheet 304 is thermally bonded to the dispersing sheet 316 and the intermediate sheet 318 in a multiplicity of areas of thermal bonding 340. As in the case of the napkin 302 illustrated in FIGS. 1 to 4, the topsheet 304, intermediate sheet 318 and backsheet 306 are thermally bonded together in an area of thermal bonding 347 extending uninterruptedly along the entire outer peripheral edge of the napkin 302. The structure other than the above-mentioned points of the napkin 302 illustrated in FIG. 7 is substantially the same as that of the napkin 2 shown in FIGS. 1 to 4.

Figure 8:
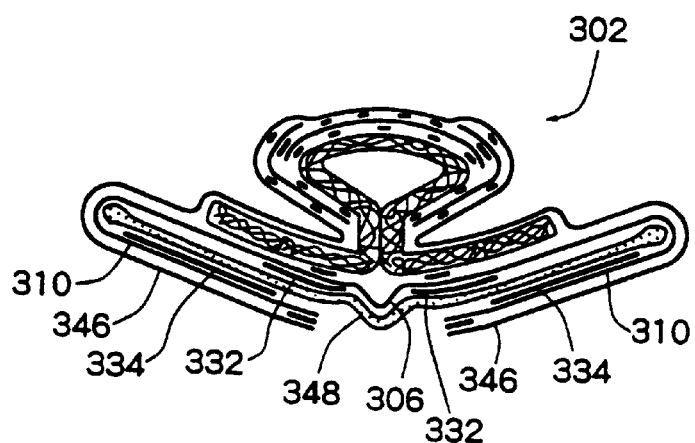
FIG. 8 is a sectional view similar to FIG. 3, showing the napkin of FIG. 7 along with part of panties in a state in which a widthwise compressive force is exerted.

With reference to FIG. 8 along with FIG. 7, the napkin 302 is also used as an overlay at a required site of the inner surface of the wearer's panties 348 (partly shown in FIG. 8). For use, the external surface of the backsheet 306 is attached strippably to the internal surface of the panties 348 via bonding means 332. A pair of wings defined by the pair of wing portions 310 of the backsheet 306, and the wing portions 346 of the topsheet 304 are folded back on the outside surface of the panties 48. The outer surfaces of the pair of wing portions 310 of the backsheet 306 are attached strippably to the outside surface of the panties 348 via bonding means 334. Assume that the wearer wears, as required, the panties 348 bearing the napkin 302 at a required site of its inner surface. When a widthwise compressive force is exerted on the napkin 302, for example, by closure of the wearer's thighs, the side core portions 314 are displaced widthwise inwardly, and caused to sink below the central core portion 312. The side core portions 314 are bonded to the panties 348 via the bonding means 332 disposed on the outer surface of the backsheet 306. The side core portions 314 are displaced attendant on the widthwise inward displacement of the panties 348, while the central core portion 312 is not directly joined to the panties 348. Thus, when a widthwise compressive force is exerted on the panties 348 and the napkin 302 by closure of the wearer's thighs, the side core portions 314 are caused to sink below the central core portion 312 fully smoothly when displaced widthwise inwardly. The sinking of the side core portions 314 below the central core portion 312 causes the central core portion 312 to be deformed in a convexly arcuate shape in a widthwise sectional view and lifted somewhat, thereby bringing the widthwise central portion of the napkin 302, i.e., its portion where the central core portion 312 exits, into intimate contact with the wearer's urogenital region. Since the side core portions 314 sink below the central core portion 312 to reduce the widthwise dimension of the napkin 302, the phenomenon that the central core portion 312 is irregularly distorted relative to the longitudinally central axis owing to the widthwise compressive force is prevented fully reliably. This leads to preclude, without fail, the undesirable event that the irregular distortion of the central core portion 312 relative to the longitudinally central axis causes the widthwise central portion of the napkin 302 to be considerably apart from the wearer's urogenital region locally, eventually leaving the wearer's urogenital region locally exposed without being covered by the napkin 302. Upon release of the widthwise compressive force that the napkin 302 has undergone, the napkin 302 is resumed to its initial state or a similar state.

A body fluid such as menses discharged from the wearer penetrates the widthwise central portion of the topsheet 304, reaching the dispersing sheet 316, where it is dispersed longitudinally, and then absorbed and held by the central core portion 12 of the absorbent core 308. Assume that a vertical compressive force as well as the widthwise compressive force may be exerted on the napkin 302, thereby bringing the outer surface of the connecting portion 313 of the absorbent core 308 into contact with the upper surface of the side core portion 312. Even in this case, the liquid impervious intermediate sheet 318 exists on the outer surface of the connecting portion 313, so that the body fluid absorbed by the central core portion 312 is not caused to flow from there into the side core portion 314 through the connecting portion 313 in its thickness direction. Even if a considerably large amount of body fluid is discharged, there is no possibility for lateral leakage in which the body fluid flows widthwise through the side core portion 314, leaking outwardly in the width direction. For some reason, a body fluid discharged from the wearer may directly drain widthwise outwardly of the widthwise central portion of the napkin 302, i.e., the portion where the central core portion 312 of the absorbent core 308 exists. Such a body fluid is absorbed by the side core portion 314, thus fully reliably preventing the accident that the body fluid leaks and soils the wearer herself or her clothing such as panties.

Figure 9:
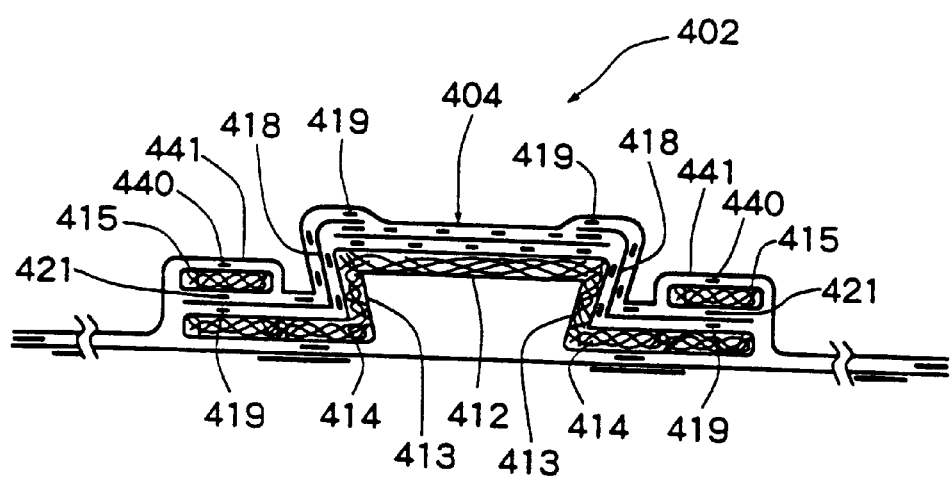
FIG. 9 is a sectional view, similar to FIG. 3, of a modified example of the napkin shown in FIG. 7.

FIG. 9 shows a modified example of the sanitary napkin 302 described above. In a napkin 402 as illustrated in FIG. 9, each of intermediate sheets 418 is caused to further extend, in a widthwise sectional view, i.e., FIG. 9, widthwise outwardly from the lower end of a connecting portion 413 of an absorbent core 408 along a side core portion 414 as far as the widthwise outward edge of the side core portion 414. Such intermediate sheet 418 is joined, using an adhesive, also to the upper surface of the side core portion 414 in a multiplicity of discrete areas of bonding 419 indicated by heavy solid lines for convenience of illustration. On that portion of each of the intermediate sheets 418 which extends on the top of the side core portion 414 is disposed an absorbent auxiliary core piece 415. Such an auxiliary core piece 415 is caused to extend longitudinally uninterruptedly throughout the length of the side core portion 414, along a widthwise outward portion of the side core portion 414 of the absorbent core 408. The lower surface of the auxiliary core piece 415 is joined, using an adhesive, to the intermediate sheet 418 in a multiplicity of discrete areas of bonding 421 indicated by heavy solid lines for convenience of illustration. The auxiliary core piece 415 itself may be formed of the same material as making up the absorbent core 408. A topsheet 404 is located above or outside the auxiliary core piece 415 in the area where the auxiliary core piece 415 exists. The topsheet 404 is thermally bonded to the upper surface of the auxiliary core piece 415 as well in a multiplicity of discrete areas of bonding 441 indicated by heavy solid lines for convenience's sake. The structure other than the above-mentioned points of the napkin 402 illustrated in FIG. 9 is substantially the same as that of the napkin 302 shown in FIGS. 7 and 8.

When undergoing a widthwise compressive force, the absorbent article of the present invention is fully reliably prevented from being distorted inappropriately. Its required site is kept on the wearer's urogenital region. Thus, the widthwise bilateral leakage of body fluids is prevented without fail. It is free from a marked increase in the manufacturing cost associated with a uselessly complicated structure.

Furthermore, when the article is in use and a compressive force is applied to the article by the legs of a wearer, each of the side core pieces tucks under the central core piece. This "tucking under" will occur for the range of compressive forces applied by a wearer when the wearer's thighs compress the article. As is shown in FIGS. 5–9, the side pieces will be tucked at least partially under the central core piece.

While particular embodiments of the present invention have been illustrated and described, it would be obvious to those skilled in the art that various other changes and modifications can be made without departing from the spirit and scope of the invention.

What is claimed is:

1. An absorbent article for maintaining close and intimate contact with the pudendal region of a female user comprising a garment facing side, a body facing side, a lateral line, a transverse line positioned perpendicularly to the lateral line, a liquid pervious topsheet, a liquid impervious backsheet having an outer surface faced adjacently with the garment facing side of the absorbent article, and an absorbent core surrounded by the topsheet and the backsheet, wherein the absorbent core includes a central core piece having a perimeter and a pair of side core pieces disposed on both sides of the central core piece, each said side core piece having an inner edge parallel to and facing the central core piece perimeter and an outer edge facing away from the central core piece perimeter, such that when a lateral compressive force is exerted upon the side core pieces, each of the side core pieces is displaced laterally toward the central core piece but caused to sink below and at least partially underneath the central core piece, said central core piece being elevated upwardly away from the compressed side core pieces being laterally compressed.

2. The absorbent article of claim 1 wherein the garment facing side of each of the side core pieces is joined to the backsheet, and on the outer surface of the backsheet is disposed, in an area extending along the garment facing sides of each of the side core pieces, a bonding means for bonding the backsheet to a garment.

3. The absorbent article of claim 2 wherein a liquid impervious intermediate sheet for preventing a liquid flow from the central core piece to each of the side core pieces is disposed between the central core piece and each of the side core pieces.

4. The absorbent article of claim 1 wherein in a state before the lateral compressive force is exerted upon the side core pieces, the inner edge of each of the side core pieces is located parallel and adjacent to the perimeter of the central core piece.

* * * * *